US008101373B2

(12) United States Patent
Wehrman et al.

(10) Patent No.: US 8,101,373 B2
(45) Date of Patent: Jan. 24, 2012

(54) β-GALACTOSIDASE DONOR FRAGMENTS

(75) Inventors: Thomas Scott Wehrman, Mountain View, CA (US); Keith R. Olson, Pleasanton, CA (US)

(73) Assignee: Discoverx Corporation, Fremont, CA (US)

( * ) Notice: Subject to any disclaimer, the term of this patent is extended or adjusted under 35 U.S.C. 154(b) by 442 days.

(21) Appl. No.: 12/249,228

(22) Filed: Oct. 10, 2008

(65) Prior Publication Data
US 2009/0098588 A1 Apr. 16, 2009

Related U.S. Application Data

(60) Provisional application No. 60/998,852, filed on Oct. 12, 2007.

(51) Int. Cl.
G01N 33/52 (2006.01)
C12Q 1/34 (2006.01)
C12N 9/38 (2006.01)
(52) U.S. Cl. ........... 435/7.6; 435/18; 435/69.7; 435/207
(58) Field of Classification Search ........................ None
See application file for complete search history.

(56) References Cited

U.S. PATENT DOCUMENTS

| | | | |
|---|---|---|---|
| 4,378,428 A | 3/1983 | Farina et al. | |
| 4,708,929 A | 11/1987 | Henderson | |
| 5,037,735 A | 8/1991 | Khanna et al. | |
| 5,106,950 A | 4/1992 | Farina et al. | |
| 5,362,625 A | 11/1994 | Krevolin et al. | |
| 5,444,161 A | 8/1995 | Manning et al. | |
| 5,464,747 A | 11/1995 | Eisenbeis et al. | |
| 5,604,091 A | 2/1997 | Henderson | |
| 5,643,734 A | 7/1997 | Henderson | |
| 6,342,345 B1 | 1/2002 | Blau et al. | |
| 6,828,099 B2 | 12/2004 | Michnick et al. | |
| 7,135,325 B2 | 11/2006 | Naqvi et al. | |
| 7,223,537 B2 | 5/2007 | Blau et al. | |
| 7,235,374 B2 * | 6/2007 | Palmer et al. | 435/7.2 |
| 2003/0175836 A1 | 9/2003 | Blau et al. | |
| 2003/0219848 A1 | 11/2003 | Naqvi et al. | |
| 2005/0287522 A1 | 12/2005 | Blau et al. | |
| 2007/0275397 A1 | 11/2007 | Wehrman et al. | |

FOREIGN PATENT DOCUMENTS
WO 9203559 A2 3/1992
(Continued)

OTHER PUBLICATIONS

F. D. Miller, et al., "A quantitative B-galactosidase a-complementation assay for fusion proteins containing human insulin B-chain peptides," Gene, 1984, vol. 29, 247-250.

(Continued)

*Primary Examiner* — Manjuanath Rao
*Assistant Examiner* — William W Moore
(74) *Attorney, Agent, or Firm* — David J. Aston; Peters Verny, LLP

(57) ABSTRACT

Truncated fragments of the small fragment of β-galactosidase are provided that have low affinity for the large fragment of β-galactosidase and provide for robust signals when two fusion proteins are complexed due to the binding of the proteins to which the β-galactosidase fragments are fused. The truncated fragments do not interfere with the complexing of the two proteins and allow for the two proteins to function and be responsive to candidate compounds that affect complex formation.

14 Claims, 4 Drawing Sheets

FOREIGN PATENT DOCUMENTS

| | | |
|---|---|---|
| WO | 9619732 A1 | 6/1996 |
| WO | 9844350 A1 | 10/1998 |
| WO | 0039348 A1 | 7/2000 |
| WO | 0071702 A1 | 11/2000 |
| WO | 0160840 A2 | 8/2001 |
| WO | 03058197 A2 | 7/2003 |
| WO | 2005113838 A2 | 12/2005 |
| WO | 2007106456 A2 | 9/2007 |

OTHER PUBLICATIONS

Michael G. Douglas, et al., "Intracellular targeting and import of an F1-ATPase B-subunit-B-galactosidase hybrid protein into yeast mitochondria," Proc. Natl. Acad. Sci. USA, Jul. 1984, vol. 81, 3983-3987.

David C. Thomas, et al., "Replication of UV-rradiated DNA in human cell extracts: Evidence for mutagenic bypass of pyrimidine dimers," Proc. Natl. Acad. Sci. USA, Aug. 1993, vol. 90, 7744-7748.

Takyuki Homma, et al., "Intraacellular Stability of alpha Fragments of B-Galactosidase: Effects of Amino-Terminally Fused Polypeptides," Biochemical and Biophysical Research Communications, Oct. 13, 1995, vol. 215, No. 2, 452-458.

William A. Mohler, et al., "Gene expression and cell fusion analyzed by lacZ complementation in mammalian cells," Proc. Natl. Acad. Sci. USA, Oct. 1996, vol. 93, 12423-12427.

Fabio Rossi, et al., "Monitoring protein-protein interactions in intact eukaryotic cells by B-galactosidase complementation," Proc. Natl. Acad. Sci. USA, Aug. 1997, vol. 94, 8405-8410.

Toufik Abbas-Terki, et al., "a-Complemented B-galactosidase: An in vivo model substrate for the molecular chaperone heat-shock protein 90 in yeast," Eur. J. Biochem, 1999, vol. 266, 517-523.

Bruce T. Blakely, et al., "Epidermal growth factor receptor dimerization monitored in live cells," Nature Biotechnology, Feb. 2000, vol. 18, 218-222.

T.S. Wehrman, et al., "A system for quantifying dynamic protein interactions defines a role for Herceptin in modulating ErbB2 interactions," Proc. Natl. Acad. Sci. USA, Dec. 12, 2006, vol. 103, No. 50, 19063-19068.

Tom Wehrman, et al., "Protein-protein interactions monitored in mammalian cells via complementation of B-lactamase enzyme fragments," Proc. Natl. Acad. Sci. USA, Mar. 19, 2002, vol. 99, No. 6, 3469-3474.

Richard M. Eglen, et al., "B-Galactosidase Enzyme Fragment Complementation as a Novel Technology for High Throughput Screening," Combinatorial Chemistry & High Throughput Screening, 2003, vol. 6, 381-387.

Tom S. Wehrman, et al., "Enzymatic detection of protein translocation," Nature Methods, Jul. 2005, vol. 2, No. 7, 521-527.

Thomas S. Wehrman, et al., "Luminescent imaging of B-galactosidase activity in living subjects using sequential reporter-enzyme luminescence," Nature Methods, Apr. 2006, vol. 3, No. 4, 295-301.

* cited by examiner

C-terminal truncations

Uninduced b-gal activity

SEQUENCE LISTING

<160> NUMBER OF SEQ ID NOS: 9

<210> SEQ ID NO 1
<211> LENGTH: 48
<212> TYPE: PRT
<213> ORGANISM: artificial
<220> FEATURE:
<223> OTHER INFORMATION: synthetic peptide

<400> SEQUENCE: 1

Asp Ser Leu Ala Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala Arg Thr Asp Arg Pro Ser Gln Gln Leu Arg
        35                  40                  45

<210> SEQ ID NO 2
<211> LENGTH: 36
<212> TYPE: PRT
<213> ORGANISM: artificial
<220> FEATURE:
<223> OTHER INFORMATION: synthetic peptide

<400> SEQUENCE: 2

Ser Leu Ala Val Val Leu Gln Arg Arg Asp Trp Glu Asn Pro Gly Val
1               5                   10                  15

Thr Gln Asn Arg Leu Ala Ala His Pro Pro Phe Ala Ser Trp Arg Asn
            20                  25                  30

Ser Glu Glu Ala
        35

<210> SEQ ID NO 3
<211> LENGTH: 35
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (1)..(4)
<223> OTHER INFORMATION: Xaa can be any naturally occurring amino acid
      as defined in the spec
<220> FEATURE:
<221> NAME/KEY: misc_feature
<222> LOCATION: (35)..(35)
<223> OTHER INFORMATION: Xaa can be any naturally occurring amino acid
      as defined in the spec

<400> SEQUENCE: 3

Xaa Xaa Xaa Xaa Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Xaa
        35

<210> SEQ ID NO 4
<211> LENGTH: 4
<212> TYPE: PRT
<213> ORGANISM: artificial
<220> FEATURE:
<223> OTHER INFORMATION: synthetic peptide

<400> SEQUENCE: 4

Ser Glu Glu Ala
1

<210> SEQ ID NO 5
<211> LENGTH: 5
<212> TYPE: PRT
<213> ORGANISM: artificial
<220> FEATURE:
<223> OTHER INFORMATION: synthetic peptide

<400> SEQUENCE: 5

Ser Glu Glu Ala Arg
1               5

<210> SEQ ID NO 6
<211> LENGTH: 36
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (1)..(4)
<223> OTHER INFORMATION: Xaa may be any naturally occurring amino acid
      as defined in the spec

<400> SEQUENCE: 6

Xaa Xaa Xaa Xaa Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu
        35

<210> SEQ ID NO 7
<211> LENGTH: 37
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (1)..(4)
<223> OTHER INFORMATION: Xaa can be any naturally occurring amino acid
      as defined in the spec

<400> SEQUENCE: 7

Xaa Xaa Xaa Xaa Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu
        35

<210> SEQ ID NO 8
<211> LENGTH: 38
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (1)..(4)
<223> OTHER INFORMATION: Xaa can be any naturally occurring amino acid
      as defined in the spec

<400> SEQUENCE: 8

```
Xaa Xaa Xaa Xaa Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala
        35

<210> SEQ ID NO 9
<211> LENGTH: 37
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (1)..(2)
<223> OTHER INFORMATION: Xaa can be any naturally occurring amino acid
      as defined in the spec

<400> SEQUENCE: 9

Xaa Xaa Val Val Leu Gln Arg Arg Asp Trp Glu Asn Pro Gly Val Thr
1               5                   10                  15

Gln Leu Asn Arg Leu Ala Ala His Pro Pro Phe Ala Ser Trp Arg Asn
            20                  25                  30

Ser Glu Glu Ala Arg
        35
```

β-GALACTOSIDASE DONOR FRAGMENTS

CROSS-REFERENCE TO RELATED APPLICATIONS

This application claims priority from U.S. Provisional Patent Application No. 60/998,852 filed on Oct. 12, 2007, which is hereby incorporated by reference in its entirety.

STATEMENT OF GOVERNMENTAL SUPPORT

None.

REFERENCE TO SEQUENCE LISTING, COMPUTER PROGRAM, OR COMPACT DISK

Applicants assert that the PDF copy of the Sequence Listing is identical to the Sequence Listing in computer readable form found on the accompanying computer text file. Applicants incorporate the contents of the sequence listing by reference in its entirety.

TECHNICAL FIELD

The field of this invention is diagnostic assays and screening.

BACKGROUND

β-Galactosidase has been a workhorse as a label for detection of a wide variety of ligands in numerous different contexts. There have been numerous applications of β-galactosidase as an intact enzyme and as fragments that when combined form an active enzyme. When fragments are used, the assay is referred to as "Enzyme Fragment Complementation" ("EFC") assay. The use of fragments can be divided into two different situations: (1) the fragments have sufficient affinity for each other that they bind independently to form an active enzyme; and (2) the fragments have a sufficiently low affinity for each other that they require an enhancement for binding, such as each of the fragments being bound to entities that do bind to each other, where when the entities bind an active enzyme is obtained. Generally, arbitrarily one of the fragments will be called an enzyme donor fragment ("ED") and the other fragment will be called an enzyme acceptor fragment ("EA"). In the case of (1) the smaller fragment is referred to as the ED.

In the first case, numerous assays have been developed where an agent is present that can inhibit the binding. In the second case, one requires that the entities bind independently or an agent is present that enhances the binding of the entities. Each of these situations has found extensive application as evidenced by the numerous patents that have issued covering the use of EFC.

Since one is dealing with an enzyme, large signal amplifications can be achieved. The signal amplification must be considered in light of the background. Even with the low affinity fragments, the relatively high concentration(s) of one or both of the fragments can result in a background signal. Depending on the nature of the assay, results can vary with different ED fragments, where the fragments may interfere with the protein to which a fragment is bound, differences may be observed between different proteins as to the degree of activity in the case of stimulation and absence of stimulation, the degree of background activity, and the like.

Small differences in structure may have significant differences as to the manner in which a fragment may be used as was observed in U.S. Patent application no. 2005/0287522. It is found that depending upon the nature of the ED, different structures can have significant effects on the utility of an assay. Therefore, it is not a matter of one structure fits all. Rather, it is found that for particular situations one ED will provide a robust assay while another will be inoperative. It has now been found that particular sequences find application in particular assays, rather than providing a universal fragment that will result in a commercially acceptable assay for all or most ligands.

RELEVANT LITERATURE

U.S. Pat. No. 7,135,325 teaches and claims the use of short EDs as providing for reduced background. This reference is incorporated herein by reference, as well as the references cited therein. U.S. Patent application serial no. 2005/0287522 describes mutated small ED fragments.

SUMMARY OF THE INVENTION

Truncated β-galactosidase enzyme donor fragments are provided that when fused to a variety of proteins and complexed to a β-galactosidase enzyme acceptor fragment result in high ratios of induced to non-induced signal and maximum induced signal to background.

BRIEF DESCRIPTION OF THE FIGURES

FIG. 1 contains SEQ ID NO:1

DESCRIPTION OF THE SPECIFIC EMBODIMENTS

Figure 1A:
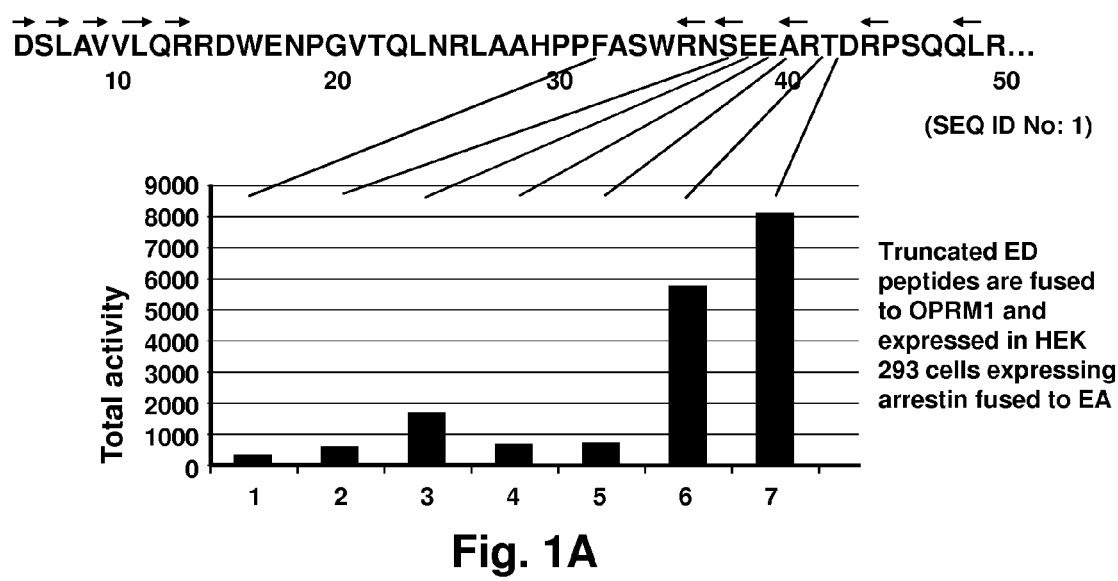
FIG. 1A is the amino acid sequence of an enzyme donor that was truncated at least one of the C and N termini. The arrows above the sequence indicate the various extents of truncation, while the lines extending from individual amino acids indicate the particular truncation for which the result is reported in the bar graph. The truncated EDs were fused to OPRM1 in HEK 293 cells expressing arrestin fused to EA.
Figure 1B:
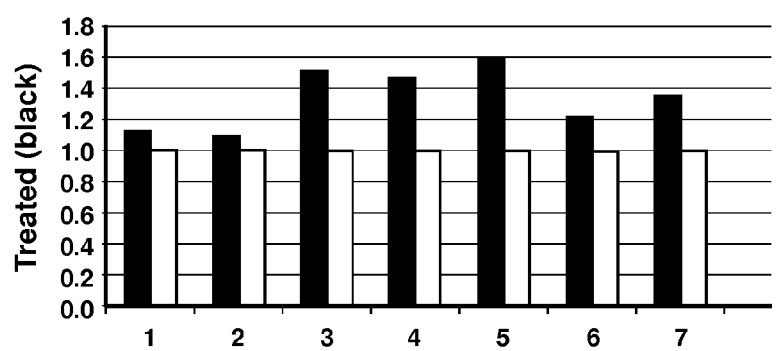
FIG. 1B is a bar graph that indicates the ratio of activity between cells untreated and treated with an agonist. Treated results are on the left bar of each pair.

Specific truncated β-galactosidase short fragments proximal to the N-terminus of *E. coli* β-galactosidase are fused to ligands for performing screening assays to detect the effect of changes in the environment on the fusion product, usually involving the screening of drugs. The fusion product of the ligand and ED serves as a surrogate for the ligand. The assays are carried out in vivo, using cells in culture. The fusion product is provided intracellularly as an expression construct, where the fusion product is expressed. To determine the effect of the change of environment, the fusion product is brought together with EA and a substrate and the formation of the enzyme product monitored. The formation of the enzyme product is related to the effect of the change of environment on the presence of the fusion product. The subject sequences are modifications of the sequence described in U.S. Pat. No. 7,135,325, S-L-A-V-V-L-Q-R-R-D-W-E-N-P-G-V-T-Q-N-R-L-A-A-H-P-P-F-A-S-W -R-N-S-E-E-A (SEQ ID NO: 2).

The truncated EDs will have the following formula:

$$\text{(SEQ ID NO: 3)}$$
$$X^1\text{-}X^2\text{-}X^3\text{-}X^4\text{-}V\text{-}V\text{-}L\text{-}Q\text{-}R\text{-}R\text{-}D\text{-}W\text{-}E\text{-}N\text{-}P\text{-}G\text{-}V\text{-}T\text{-}Q\text{-}L\text{-}N\text{-}R\text{-}L\text{-}A\text{-}A\text{-}H\text{-}P\text{-}P\text{-}F\text{-}A\text{-}S\text{-}W\text{-}R\text{-}N\text{-}X^5$$

wherein $X^5$ is S-E;

S-E-E;

S-E-E-A;   (SEQ ID NO: 4)
or

S-E-E-A-R;   (SEQ ID NO: 5)

$X^1$ is D or is absent;
$X^2$ is S or is absent;
$X^3$ is L or is absent; and
$X^4$ is A or is absent.

$X^{1-4}$ are present when $X^5$ is S-E; -S-E-E; and S-E-E-A (SEQ ID NO: 4) and $X^{3-4}$ are present when $X^5$ is S-E-E-A-R (SEQ ID NO: 5). It is found that these compounds provide high ratios of induced signal to uninduced signal and maximum induced signal to background with a wide variety of protein ligands. Furthermore, their small size does not interfere with the protein function of the fusion product acting as a surrogate for the ligand intracellularly.

The ED is used with the EA to form an active β-galactosidase enzyme that can be detected by the addition of a detectable substrate, normally a colored, fluorescent or chemiluminescent substrate. b-galactosidase uses effectively fluorescers having phenolic groups that are etherified with a β-galactosyl group. The common substrates are β-D-galactopyranosyl phenols, such as fluorescein, mono- and di-substituted, 4-methoxycarbonyl-butyloxy-fluorescein, o-nitrophenyl β-D-galactoside, β-methylumbelliferyl β-D-galactoside, X-gal, resorufin β-D-galactoside, commercially available oxetanes, e.g., Galacto-Light Plus® kits (chemiluminescence) and chlorophenol red. The di-β-D-galactopyranosylfluorescein, and chlorophenol red-β-D-galactopyranoside may be used as intracellular markers.

The ED may be prepared by any convenient means. The ED will usually be expressed from an expression construct having a sequence encoding ED fused to another protein, under the transcriptional and translational control of a promoter region that may include one or more enhancers and well as the coding for initiation of translation. The regulatory regions will be chosen so as to be competent in the cell being transformed. The expression construct may be inserted into the genome and added transiently as a virus, bare DNA or the like.

The ED may be joined to any polypeptide of interest, where the ED will serve as a label, where the polypeptide may be wild-type, mutant or a designed sequence.

The EDs of the subject invention find particular application in conjunction with polypeptides, e.g., oligopeptides and proteins, where it is undesirable for the ED and the EA to have a high binding affinity. That is, the EDs, because of their smaller size are less likely to interfere with the function of the fused polypeptide. Where degradation is of interest, the ED will be rapidly degraded so as to diminish background and is less likely to adversely affect intracellular movements and interactions. One illustration is WO 00/039348, which describes fusion proteins comprising an ED marker for determining solubility and folding of the fusion protein. By employing the substantially smaller EDs of the subject invention, the experience with the fusion protein is more likely to closely emulate the experience with the natural protein.

The fusion proteins of the subject invention find application for intracellular events, including translocation, degradation, secretion, complex formation, post-translational modification, etc. Where one is interested in degradation of the fusion protein, the degradation of the fusion protein substantially eliminates background. For translocation, the smaller ED is less likely to interfere with the interaction of the natural protein with the other proteins involved with the translocation and, as applicable, crossing an organelle membrane. Similarly, for complex formation, the smaller ED is less likely to significantly change the affinity of the fusion protein for its binding partner. In some instances the two proteins will be binding partners, that is, naturally binding to each other to form a complex. In other instances the two proteins may require an additional compound that serves as a bridge to bring the two proteins together to form a ternary complex.

A number of patent applications have been filed using EDs for a variety of purposes. These applications include U.S. patent application Ser. Nos. 10/229,747; 10/353,280; 10/398,320 and 11/170,123, all of which are incorporated herein by reference. The subject truncated EDs can be used for intracellular and extracellular detection, using intact cells, as well as lysates, or in vitro assays. The subject EDs may be used for intracellular protein interactions where the proteins are found in the same compartment, such as the cytosol, in an organelle, such as the nucleus, mitochondrion, etc., associated with a membrane, such as the cell membrane, nuclear membrane, endoplasmic reticulum, or the like.

For the preparation of the fusion protein and its expression construct, conventional splicing and insertion techniques are employed. The ED may be at the C-terminus, the N-terminus or both or internal to the fusion protein. Therefore, there may be one or more ED sequences in the fusion protein to enhance the number of ED units present per fusion protein to increase the observed signal with the fusion protein molecules present. The ED will come from the N-terminus of the β-galactosidase enzyme The fusion proteins will usually be selected to provide a functional protein that is soluble, does not aggregate so as to be unavailable for complexing, has substantially the natural folding, so as to be susceptible to binding to endogenous proteins that normally complex to the polypeptide fused to the ED, will be susceptible to the same proteases that such polypeptide is susceptible and will usually be able to perform substantially the same functions that such polypeptide performs. Therefore, the polypeptide is capable of acting as a surrogate for the natural protein to allow for measurements that are predictive of the activity of the natural protein.

The particular site of the ED in the fusion protein will depend upon the ability to include the ED in the coding sequence without significant reduction in the natural activity of the protein of interest. Thus, depending upon how much is known about the protein of interest, its structure, site(s) of binding to other entities, the folding pattern, as to loops, β-sheets and α-helices, the manner in which the ED activity will be modulated, e.g., degradation, steric interference of binding with EA by another entity, modification resulting in changes in conformation or charge, etc., the ED will be situated to provide the optimized response. For degradation, it will frequently not matter at what site the ED is situated, this is also likely to be true in many cases for steric interference, so long as the protein of interest retains its natural conformation and susceptibility to degradation and the ED retains its ability to activate the EA. However, for localized modification, such as phosphorylation or dephosphorylation, proteolytic cleavage for maturation, etc., it may be desirable to have the ED in proximity to the modified site. By knowing the structure of the protein, one can select loops, α-helices, β-sheets, sites of binding or the like to determine the site for insertion of the ED.

The ED may be inserted into the coding region in a variety of ways. For a cDNA gene, one may select a suitable restriction site for insertion of the sequence, where by using overhangs at the restriction site, the orientation is provided in the correct direction and in the correct frame so that a fusion protein is produced. Alternatively, one may use constructs that have homologous sequences with the target gene and allow for homologous recombination, where the homologous sequences that are adjacent in the target gene are separated by the ED in the construct. By using a plasmid in yeast having the cDNA gene, with or without an appropriate transcriptional and translational regulatory region, one may readily insert the ED construct into the cDNA gene at an appropriate site. Alternatively, one may insert the ED coding region with the appropriate splice sites in an intron or in an exon of the gene encoding the protein of interest. In this way, one can select for a site of introduction at any position in the protein. In some instances, it will be useful to make a number of constructs, where the ED is introduced into an intron and test the resulting proteins for ED activity and retention of function of the protein. Various other conventional ways for inserting encoding sequences into a gene can be employed. For expression constructs and descriptions of other conventional manipulative processes, See, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins EDs. (1985)]; "Transcription And Translation" [B. D. Hames & S. J. Higgins, EDs. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The fusion protein may have a protease recognition sequence, where the ED is released upon cleaving of the recognition sequence. The changes in the activity of the ED can be a result of the degradation of the fusion protein, by ubiquitination followed by degradation, protease degradation, denaturation, or other process. Alternatively, activity can be modified as a result of complex formation between the protein of interest and another protein, intra- or extracellular. Activity can also be modified due to modification of the fusion protein, where the modification may result in complexing with another protein, change in the fusion protein conformation, presence of a substituent that changes the activity of the ED, or the like. Also, transport of the fusion protein to a compartment in the cell can result in a change in the measurable activity of the ED. In addition, where the modification affecting the ED activity is part of a pathway, the change in ED activity can be related to the events in the pathway. The fusion protein may comprise a protein of interest, a fragment of the protein of interest, a different polypeptide to represent the protein of interest or may be an intermediate for measuring some other protein or other activity, so long as the observed signal is related to the event of interest.

Protein transport or translocation in the cell from the cytoplasm to another organelle or site, e.g., nucleus, cell membrane, proteasome, mitochondria, lysozome, Golgi, etc., can be of great importance to the biological properties of the protein and the cellular pathways of the cell. For protein transport, one can use leader sequences at the N terminus of the fusion protein from proteins that are known to be translocated to particular sites, e.g., NLS and NRS for nuclear translocation. One may also use coding sequences that result in modification of the fusion protein for binding the fusion protein to the cell membrane, such as sequences resulting in prenylation, myristoylation, farnesylation, etc. By providing for EA and substrate in the cell or in a lysate, depending upon the site of the fusion protein, one may be able to detect the presence of the fusion protein at the particular site. Alternatively, one may isolate organelles or part of the cell, e.g., microsomes, to determine the amount of the fusion protein associated with the cellular component.

By having the native target protein as a fusion protein in its natural environment in a cell of interest, one can observe the natural effect of changes in the cell as a result of maturation, differentiation, changes in environment, and the like on the level of the protein in the cell. With embryonic stem cells, one can observe the variation in amount of the target protein over time as the cells undergo differentiation and expansion. The presence of the ED fused to a protein involved with foetal development, e.g., Hox proteins, morphogens, BMPs, homeobox proteins, etc., allows one to readily analyze for the expression of the proteins, the concentration level in the medium or intracellular, the changes in the concentration during differentiation, the level of gradients of such proteins, and the like. Therefore, the ED can serve as an important research tool in elucidating the various mechanisms and pathways involved in the foetal cell development.

While the subject invention permits detection of events intracellularly, in some situations it will be necessary to lyse the cells and do the determination extracellularly. In this situation, either intact organelles or microsomes may be isolated, or the cell contents, particularly the cytoplasmic contents, isolated. The lysate may then be analyzed in accordance with conventional ways, adding EA, substrate and an appropriate buffer and measuring the signal.

Of the protein categories of interest, transcription factors, inhibitors, regulatory factors, enzymes, membrane proteins, structural proteins, and proteins complexing with any of these proteins, are of interest. Specific proteins include enzymes, such as the hydrolases exemplified by amide cleaving peptidases, such as caspases, thrombin, plasminogen, tissue plasminogen activator, cathepsins, dipeptidyl peptidases, prostate specific antigen, elastase, collagenase, exopeptidases, endopeptidases, aminopeptidase, metalloproteinases, including both the serine/threonine proteases and the tyrosine proteases; hydrolases such as acetylcholinesterase, saccharidases, lipases, acylases, ATP cyclohydrolase, cerebrosidases, ATPase, sphingomyelinases, phosphatases, phosphodiesterases, nucleases, both endo- and exonucleases; oxidoreductases, such as the cytochrome proteins, the dehydrogenases, such as NAD dependent dehydrogenases, xanthine dehydrogenase, dihydroorotate dehydrogenase, aldehyde and alcohol dehydrogenase, aromatase; the reductases, such as aldose reductase, HMG-CoA reductase, trypanothione reductase, etc., and other oxidoreductases, such as peroxidases, such as myeloperoxidase, glutathione peroxidase, etc., oxidases, such as monoamine oxidase, myeloperoxidases, and other enzymes within the class, such as NO synthase, thioredoxin reductase, dopamine beta.-hydroxylase, superoxide dismutase, nox-1 oxygenase, etc.; and other enzymes of other classes, such as the transaminase, GABA transaminase, the synthases, .beta.-ketoacyl carrier protein synthase, thymidylate synthase, synthatases, such as the amino acid tRNA synthatase, transferases, such as enol-pyruvyl transferase, glycinamide ribonucleotide transformylase, COX-1 and -2, adenosine deaminase.

Kinases are of great significance, such as tyrosine kinases, the MAP kinases, the cyclin dependent kinases, GTP kinases, ser/thr kinases, Chk1 and 2, etc.

Also of interest are enzyme inhibitors, such as .alpha.-.sub.1-antitrypsin, antithrombin, cyclophilin inhibitors, proteasome inhibitors, etc.

Neuronal proteins, such as .beta.-amyloid, TNF, prion, APP, transporters, e.g., dopamine transporter, receptors, such as NMDA receptors, AMDA receptors, dopamine receptors, channels, etc.

Another class of proteins is the transcription factors and their inhibitors or regulatory proteins, such as Adr Ace, Amt, AP, Atf, Att, Baf, Brn, Btf, C Ebp, C Jun, C Ets, CREB, CF, Chop, DP, E2F, Elk, Gata, Hnf, Iii A-H, Irf, NY Y, Otf, NFκB, NF-AT, Oct-1, Pea, Pit, PU, S, SP, Stat, Tef, TFIII, TFIIII, Ubf and Usf, while the inhibitors include Erk, IκB, LIF, Smad, RANTES, Tdg, etc., as well as other proteins associated with pathways that induce transcription factor synthesis, activation or inhibition.

In some instances, housekeeping proteins will be of interest, such as the proteins involved in the tricarboxylic acid cycle, the Krebs cycle, glycogenesis, etc.

As indicated previously, the genes of each of these proteins may be manipulated in numerous ways to fuse ED with the protein while maintaining the biological activity of the protein and ED.

Other proteins of interest are the oncogenes, such as Src, Ras, Neu, Erb, Fos, Kit, Jun, Myc, Myb, Abl, Bcl, etc. Cytokines, such as the interferons, α-ξ, interleukins, 1-19, and integrins, adhesins, TNF, receptors, hormones, colony stimulating factors, growth factors, such as epidermal growth factor, fibroblast growth factor, etc., bone morphogenetic proteins, developmental proteins, such as the Hox proteins, or other proteins binding to or regulating proteins binding to homeoboxes, e.g., the hedgehog proteins, basement membrane proteins, heat shock proteins, proteins containing Krupple and Kringle structures chaperoning, calcium associated proteins, e.g., calmodulin, calcineurin, etc., membrane channels, transporter proteins, etc.

Also of interest are the proteins associated with proliferation, such as the cyclins, cyclin dependent kinases, p53, RB, etc.

For each of the applications using the EDs of the subject invention, kits can be provided having a source of EA, either as the protein or an expression construct for cellular introduction, a source of ED, as itself or as a fusion protein, again as the protein itself or as an expression construct for cellular introduction, a conjugate with other than a polypeptide, one or more substrates, buffer, and other reagents.

As indicated previously, the genes of each of these proteins may be manipulated in numerous ways to fuse ED with the protein while maintaining the biological activity of the protein and ED.

In performing assays with cells, cells are employed that are capable of expressing the ED fusion protein and desirably the EA fusion protein. Cells will be added to an appropriate medium at a convenient density, usually in the range of about $1 \times 10^3$ to $1 \times 10^5$, depending upon the volume of the assay and the specific reagents being assayed.

The following examples are intended to illustrate but not limit the invention.

EXPERIMENTAL

The following are the directions for performing the determinations of the response to inducing agents and comparing the prior art ED (pK1) to an ED of the subject invention (pK2):

The cells used were HEK293 and CHOK1 cells. Following substantially the procedures described in U.S. patent application Ser. No. 10/229,247, filed Aug. 27, 2002, and U.S. patent application Ser. No. 11/132,764 (Publication no. 2005/0287522), filed May 18, 2005, whose disclosures are specifically incorporated by reference, each of the cell lines was infected with retroviral constructs. The viral plasmid was the PLNCX2 vector from Clontech. The plasmid includes sufficient retroviral sequences to enable viral production in the appropriate packaging cell lines. The plasmid also includes the neomycin antibiotic resistance gene and a CMV promoter that is used to drive expression of the target ED fusion. The entire GPCR coding regions were cloned downstream of the CMV promoter and upstream of the ED to encode a GPCR-ED fusion to provide cells having β-arrestin2 fused to EA and selected by the antibiotic resistance marker hygro and the ED constructs described below selected by the antibiotic resistance marker NEO. The ED is fused at the intracellular terminus, i.e., C-terminus of the proteins.

Preparation of Detection Reagents—The detection reagents must be prepared as a working solution prior to use, and once prepared are stable for at least 24 hours at room temperature with no impact on assay performance. The detection reagents consist of the substrate and co-factors for chemiluminescence signal detection, as well as the reagents necessary for selective cell permeabilization. Working solution is prepared by combining PathHunter™ Cell Assay Buffer (DiscoveRx, Inc., Fremont, Calif.), Galacton Star® and Emerald II® reagent to 25 μl of cells+compound. reagents (ABI, Bedford, Mass.) at a ratio of 19:1:5. Sufficient reagent is provided in each kit to perform the indicated number of assays in a 384-well, full-volume microplate assuming an addition of 12 μl of detection reagent per well or in a 96-well, full-volume microplate assuming an addition of 50 μl of detection reagent per well.

The table below outlines the procedure for using the PathHunter™ Detection Kit to monitor protein translocation in a either a parental PathHunter cell line transfected with a target protein of interest, or one of the dedicated PathHunter cell lines available from DiscoveRx for monitoring specific protein translocation events (i.e., glucocorticoid receptor).

TABLE 1

Assay Procedure

| Steps | Volumes (384-well full volume) | Volumes (96-well full volume) |
|---|---|---|
| Step 1: Plate Cells & Incubate Overnight | Add 25 μl of cells in each well at a preferred density of 5000-25,000 cells per well. | Add 100 μl of cells in each well at a preferred density of 10,000-30,000 cells per well. |

TABLE 1-continued

Assay Procedure

| Steps | Volumes (384-well full volume) | Volumes (96-well full volume) |
|---|---|---|
| Step 2: Treat Cells | Dissolve compounds in vehicle of choice and add 1-5 µl per well at a temperature of 37° C. to achieve desired amount. Do not exceed 2% DMOS. | Dissolve compounds in vehicle of choice and add 5-20 µl per well at a temperature of 37° C. to achieve desired amount. Do not exceed 2% DMSO. |
| Step 3: Add Detection Reagents | Following desired incubation time of about 60-90 min, add 12 µl of detection reagents per well. | Following desired incubation time of about 60-90 min, add 50 µl of detection reagents per well. |
| Step 4: Read Samples | Samples can be read on any standard luminescence plate reader after 30-60 minutes incubation. | Samples can be read on any standard luminescence plate reader after 30-60 minutes incubation. |

The following table indicates the results.

TABLE 2

| Receptor | PK | Basal Activity | Fold induct. | ligand |
|---|---|---|---|---|
| CCR4 | PK1 | 1100 | 18.9 | CCL22 |
| CCR4 | PK2 | 5000 | 3 | CCL22 |
| CCR6 | PK2 | 3200 | 6.5 | CCL20 |
| CCR6 | PK1 | 220 | 1.4 | CCL20 |
| CHRM2 | PK1 | 140 | 1.6 | Oxotremorine |
| CHRM2 | PK2 | 340 | 6.1 | Oxotremorine M |
| CRHR2 | PK1 | 1000 | 13.1 | Sauvagine |
| CRHR2 | PK2 | 9000 | 17.4 | Sauvagine |
| CRTH2 | PK1 | 430 | none | Prostaglandin D2 |
| CRTH2 | PK2 | 30000 | 2.6 | Prostaglandin D2 |
| MC3R | PK1 | 130 | none | aMSH |
| MC3R | PK2 | 2700 | 3.2 | aMSH |
| OPRM1 | PK2 | 820 | 8.3 | Enkephalin |
| OPRM1 | PK1 | 400 | 26.8 | Enkephalin |
| P2RY6 | PK1 | 1000 | 1.3 | UDP |
| P2RY6 | PK2 | 5600 | 1.9 | UDP |
| PTHR2 | PK1 | 180 |  | PTHRP |
| PTHR2 | PK2 | 1400 | 2.8 | TIP39 |
| PTHR2 | PK2 | 500 | none | PTHRP |
| PTHR2 | PK2 | 1400 | 72.9 | PTH (1-34) |
| SALPR | PK1 | 1000 | none | Relaxin-3 |
| SALPR | PK2 | 15000 | 1.8 | Relaxin-3 |
| SSTR1 | PK1 | 300 | 1 | Somatostatin-14 |
| SSTR1 | PK1 | 300 | 1.2 | Somatostatin-28 |
| SSTR1 | PK1 | 180 | 1 | TYR-SRIF14 |
| SSTR1 | PK2 | 4800 | 2.2 | [TYR1] Somatostatin 14 |
| SSTR1 | PK2 | 2700 | 1.5 | Somatostatin 14 |
| SSTR1 | PK2 | 3000 | 1.3 | Somatostatin 28 |
| SSTR4 | PK1 | 1300 | 1.5 | Somatostatin-14 |
| SSTR4 | PK1 | 1600 | 1.3 | Somatostatin-28 |
| SSTR4 | PK1 | 1300 | 1.8 | L803,087 |
| SSTR4 | PK2 | 14000 | 2.1 | L803,087 |
| SSTR4 | PK2 | 11000 | 1.6 | Somatostatin 14 |
| SSTR4 | PK2 | 10000 | 1.6 | Somatostatin 28 |

The first column indicates the receptor. The second column indicates whether PK1 or PK2 was employed as the ED fusion partner. The basal activity indicates the signal in the absence of stimulation. The fourth column indicates the fold induction for each of the constructs, where saturating conditions of the ligand were employed. The fifth column indicates the ligand that was employed.

It should be noted that a 5-fold induction is sufficient for performing an assay, so that inductions greater than 5-fold are not significant. Desirably the induction should be at least 1.2-fold, usually at least about 1.5-fold and preferably at least about 2-fold. As evidenced from the above table, usually PK2 provides a better result and occasionally PK1, depending upon the protein to which it is fused. Therefore, in performing assays, where PK2 is inadequate to provide a signal, PK1 would be investigated. It is noteworthy that PK1 did not provide a signal with the proteins CRTH2, MC3R, PTHR2 and SALPR. By way of contrast, PK2 provided a signal with every protein under the described assay conditions.

Figure 2:
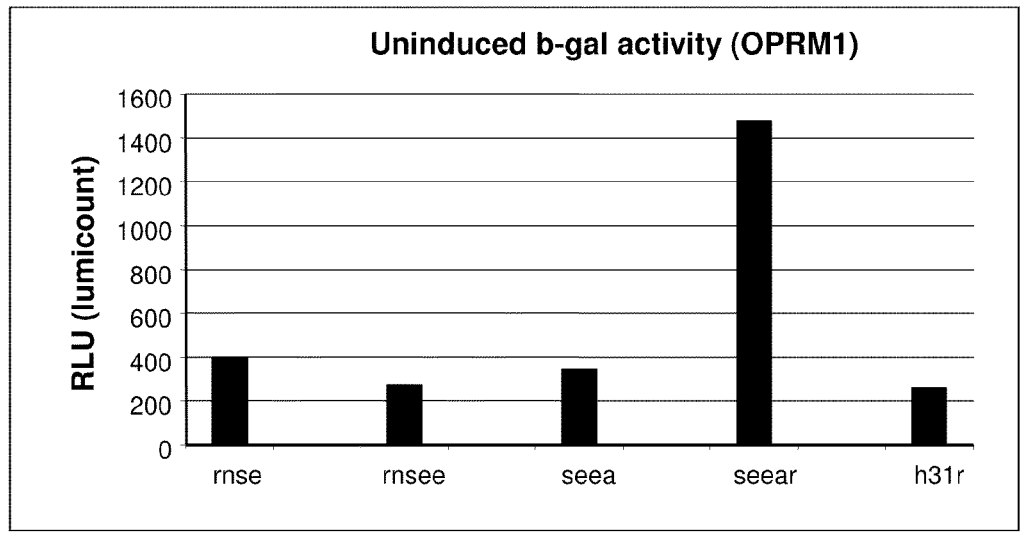
FIG. 2 has two bar graphs, the upper bar graph compares the activity of β-galactosidase activity in the cells in the absence of an agonist, where ED is fused to OPRM1 and EA fused to arrestin, while the lower bar graph shows the uninduced β-galactosidase activity in the cells in the absence of an agonist where the ED is fused to secretin receptor (SCTR). The truncation for each of the EDs is indicated by the C-terminus amino acids.
Figure 2:
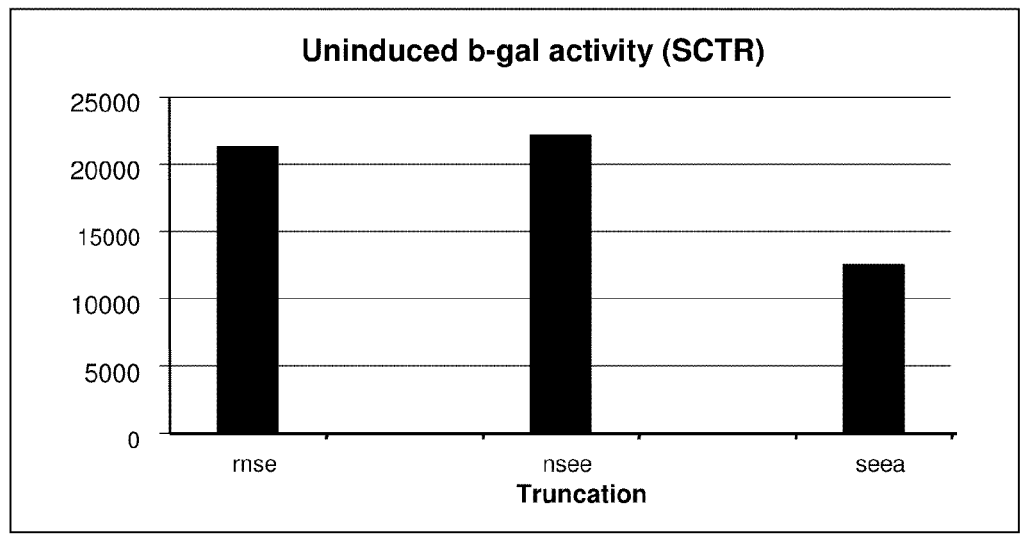
Figure 3:
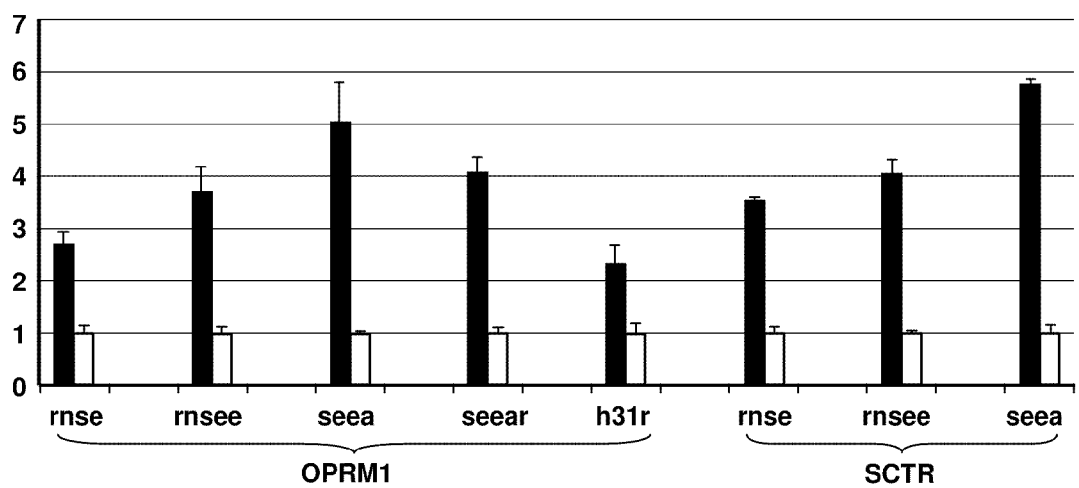
FIG. 3 is a bar graph of fusions of truncated EDs fused to OPRM1 or SCTR where 293 A2 cells were infected with the gene construct expressing the fusion proteins and the fold induction with an agonist indicated. A comparison of the prior art mutated ED h31r is also shown. Treated results are on the left bar in each pair.
Figure 4:
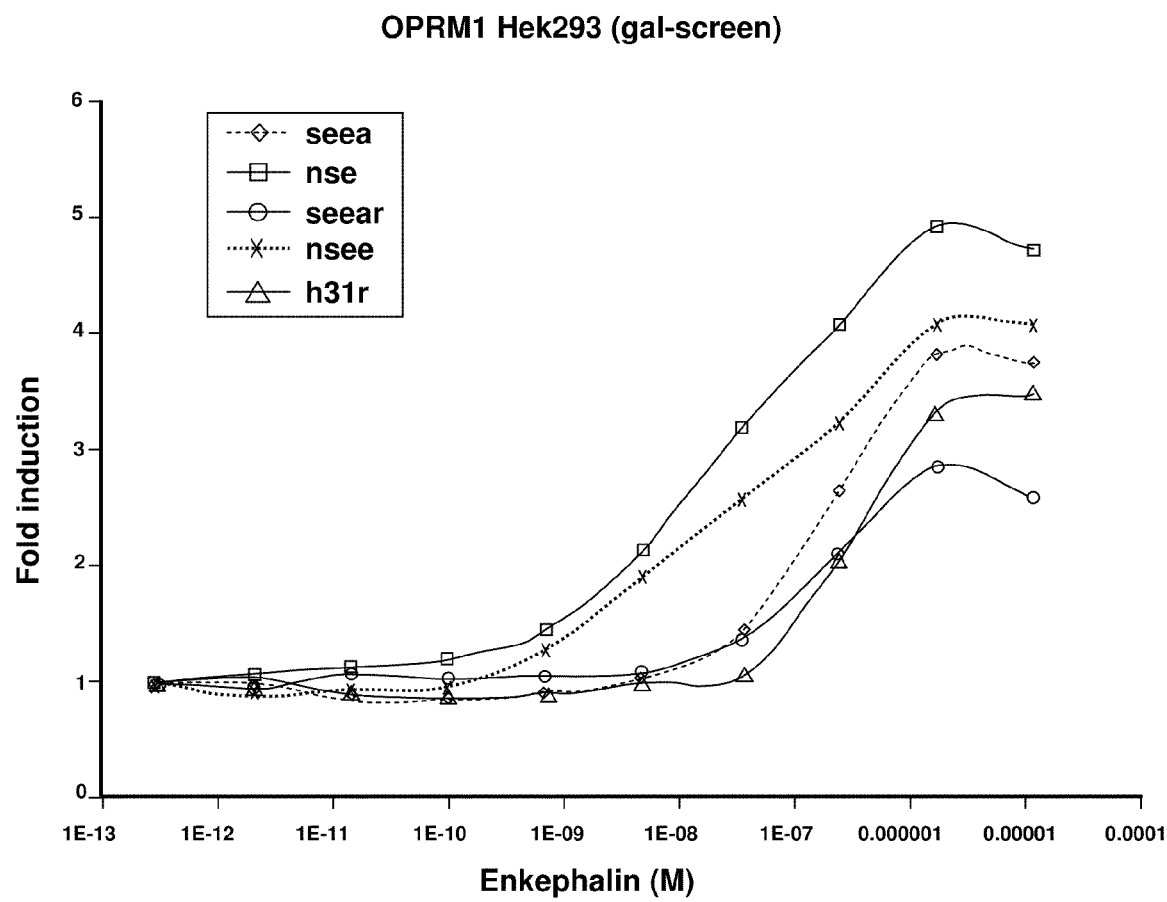
FIG. 4 is a comparison graph showing the fold induction for the different constructs with the C terminus of the truncated ED indicated with the prior art h31r shown for comparison. The graph shows fold induction as the ordinate and the concentration of the agonist enkephalin as the abscissa.

In addition, as is observed in FIG. 1a, the truncated ED peptides of this invention provide for low background activities and substantial increases in signal when induced. See also, FIGS. 2 and 3. FIG. 4 shows a graph of the response with variation in concentration of the ligand enkephalin with the fusion of OPRM1 and the different truncated EDs as compared to the mutated literature ED H31R. While the prior art ED requires greater than about 1E-07M of enkephalin to obtain an induced signal, an induced signal can be observed at 1E-09M with two of the subject EDs.

The above results demonstrate that selected EDs that are smaller than the mutated H31R in the literature can provide for enhanced signals when fused to a great variety of proteins. The subject EDs differ from the prior art EDs, which either are larger or are mutated providing for substantial advantages. The low affinity of the EDs makes the complex formation to form β-galactosidase dependent upon the complex formation of the proteins to which ED and EA are individually attached. This provides for substantially lower background. The small size of the EDs diminishes the interference with the binding of the GPCRs and arrestin, so as to provide for a more robust assay. Also, in the case of degradation, the small size of the EDs will result in the rapid degradation of the EDs avoiding the presence of EDs that could contribute to background signal. In addition, the subject EDs have low affinity for EA, but when the ligand for the receptor, e.g., arrestin binds to a GPCR, bringing the ED and EA in proximity, the two fragments are able to provide a robust signal substantially greater than in the absence of binding of the ligand to the receptor. In this way, one can screen compounds for their effect on the binding of a ligand to a receptor, particularly where binding results in the recruitment of a third entity to the receptor. For example, in the case of GPCRs that recruit arrestin when activated by a ligand, by having ED fused to the receptor and EA fused to the arrestin, activation of the GPCR results in bringing together the ED and the EA to provide a signal indicating that the compound of interest is able to activate the GPCR.

All references referred to in the text are incorporated herein by reference as if fully set forth herein. All procedures disclosed in the references are incorporated as demonstrating the level of skill in the art to perform the procedures indicated in this application. The relevant portions associated with this document will be evident to those of skill in the art. Any discrepancies between this application and such reference will be resolved in favor of the view set forth in this application.

Although the invention has been described with reference to the above examples, it will be understood that modifications and variations are encompassed within the spirit and scope of the invention. Accordingly, the invention is limited only by the following claims.

What is claimed is:

1. An in vitro method for determining the effect of an intracellular environment on the binding of first and second proteins, where said first protein is fused to an enzyme donor fragment and said second protein is fused to an enzyme acceptor fragment, said enzyme acceptor and enzyme donor are fragments of β-galactosidase and said enzyme donor fragment is one of
   (a) $X^1$-$X^2$-$X^3$-$X^4$-V-V-L-Q-R-R-D-W-E-N-P-G-V-T-Q-L-N-R-L-A-A-H-P-P-F-A-S-W-R-N-S-E (SEQ ID NO:6),
   (b) $X^1$-$X^2$-$X^3$-$X^4$-V-V-L-Q-R-R-D-W-E-N-P-G-V-T-Q-L-N-R-L-A-A-H-P-P-F-A-S-W-R-N-S-E-E (SEQ ID NO:7), or
   (c) $X^3$-$X^4$-V-V-L-Q-R-R-D-W-E-N-P-G-V-T-Q-L-N-R-L-A-A-H-P-P-F-A-S-W-R-N-S-E-E-A-R (SEQ ID NO:9), wherein
      $X^1$ is D or is absent;
      $X^2$ is S or is absent;
      $X^3$ is L or is absent; and
      $X^4$ is A or is absent;
   said method comprising:
      exposing said proteins to said environment in vitro;
      adding to said proteins a β-galactosidase substrate providing a detectable signal; and
      determining said signal, where said signal is related to the effect of said environment on the binding of said first and second proteins.

2. A method according to claim 1, wherein said first and second proteins are binding partners.

3. A method according to claim 1, wherein said environment comprises a candidate compound of interest.

4. A method according to claim 1, wherein said β-galactosidase substrate provides a chemiluminescent signal.

5. A method according to claim 1, wherein the induced signal with a ligand for said second protein is at least 1.2-fold the signal in the absence of said ligand.

6. An in vitro method for determining the effect of an extracellular environment on the binding of first and second proteins, where said first protein is a receptor to which an enzyme donor is joined at an intracellular terminus and said second protein is an intracellular protein and is joined to an enzyme acceptor and recruited when said first protein is activated, whereby an active enzyme is formed, said enzyme acceptor and enzyme donor are fragments of β-galactosidase and said enzyme donor fragment is one of
   (a) $X^1$-$X^2$-$X^3$-$X^4$-V-V-L-Q-R-R-D-W-E-N-P-G-V-T-Q-L-N-R-L-A-A-H-P-P-F-A-S-W-R-N-S-E (SEQ ID NO:6),
   (b) $X^1$-$X^2$-$X^3$-$X^4$-V-V-L-Q-R-R-D-W-E-N-P-G-V-T-Q-L-N-R-L-A-A-H-P-P-F-A-S-W-R-N-S-E-E (SEQ ID NO:7), or
   (c) $X^3$-$X^4$-V-V-L-Q-R-R-D-W-E-N-P-G-V-T-Q-L-N-R-L-A-A-H-P-P-F-A-S-W-R-N-S-E-E-A-R (SEQ ID NO:9), wherein
      $X^1$ is D or is absent;
      $X^2$ is S or is absent;
      $X^3$ is L or is absent; and
      $X^4$ is A or is absent;
   said method comprising:
      exposing a cell to said environment in vitro, said first and second proteins being expressed in said cell;
      lysing said cell to form a lysate;
      adding to said lysate a β-galactosidase substrate providing a detectable signal; and
      determining said signal, where said signal is related to the effect of said environment on the binding of said first and second proteins.

7. A method according to claim 6, wherein said first protein is a G protein-coupled receptor.

8. A method according to claim 6, wherein said first and second proteins comprise, respectively, a G protein-coupled receptor and arrestin.

9. A fusion protein comprising at least a functional fragment of a protein fused at an intracellular terminus to a β-galactosidase enzyme donor fragment of the formula:

$X^1$-$X^2$-$X^3$-$X^4$-V-V-L-Q-R-R-D-W-E-N-P-G-V-T-Q-L-N-R-L-A-A-H-P-P-F-A-S-W-R-N-S-E (SEQ ID NO:6), wherein $X^1$ is D or is absent;
$X^2$ is S or is absent;
$X^3$ is L or is absent; and
$X^4$ is A or is absent.

10. A fusion protein comprising at least a functional fragment of a protein fused at an intracellular terminus to a β-galactosidase enzyme donor fragment of the formula:

$X^1$-$X^2$-$X^3$-$X^4$-V-V-L-Q-R-R-D-W-E-N-P-G-V-T-Q-L-N-R-L-A-A-H-P-P-F-A-S-W-R-N-S-E-E (SEQ ID NO:7), wherein $X^1$ is D or is absent;
$X^2$ is S or is absent;
$X^3$ is L or is absent; and
$X^4$ is A or is absent.

11. A fusion protein comprising at least a functional fragment of a protein fused at an intracellular terminus to a β-galactosidase enzyme donor fragment of the formula:

$X^3$-$X^4$-V-V-L-Q-R-R-D-W-E-N-P-G-V-T-Q-L-N-R-L-A-A-H-P-P-F-A-S-W-R-N-S-E-E-A-R (SEQ ID NO:9), wherein $X^1$ is D or is absent;
$X^2$ is S or is absent;
$X^3$ is L or is absent; and
$X^4$ is A or is absent.

12. The protein according to claim 9, wherein the functional fragment is a functional fragment of a G protein-coupled receptor.

13. The protein according to claim 10, wherein the functional fragment is a functional fragment of a G protein-coupled receptor.

14. The protein according to claim 11, wherein the functional fragment is a functional fragment of a G protein-coupled receptor.

* * * * *